United States Patent [19]

Ogata et al.

[11] Patent Number: 5,096,763
[45] Date of Patent: Mar. 17, 1992

[54] MAGNET ARTICLE FOR ATTRACTING FOREIGN MATTERS IN THE STOMACH

[75] Inventors: Masao Ogata, Honjyo; Nobuo Kakinuma, Hanyu, both of Japan

[73] Assignee: 501 Hitachi Metals. Ltd., Tokyo, Japan

[21] Appl. No.: 650,584

[22] Filed: Feb. 5, 1991

[30] Foreign Application Priority Data

Feb. 7, 1990 [JP] Japan ............................. 2-11405[U]

[51] Int. Cl.⁵ .......................... A61B 19/00; A61N 1/42
[52] U.S. Cl. ...................................... 428/76; 428/900; 600/12; 335/303
[58] Field of Search ............................ 428/76, 68, 900; 600/12; 335/303

[56] References Cited

U.S. PATENT DOCUMENTS

| | | | |
|---|---|---|---|
| 3,187,239 | 6/1965 | Rosenberger et al. | 600/12 |
| 4,303,062 | 12/1981 | Vars | 600/12 |
| 4,888,068 | 12/1989 | Tokunaga et al. | 148/104 |

FOREIGN PATENT DOCUMENTS 60-61703 4/1981 Japan .
57-53550 11/1982 Japan .

*Primary Examiner*—Alexander S. Thomas
*Attorney, Agent, or Firm*—Finnegan, Henderson, Farabow, Garrett & Dunner

[57] ABSTRACT

The magnet article for attracting foreign matters in the stomach is constituted by (a) a hollow cylindrical case made of a corrosion-resistant, non-magnetic material: (b) a plurality of disc-shaped yokes made of a soft magnetic material; (c) a plurality of disc-shaped magnet members made of an R-Fe-B permanent magnet material and having magnetic poles on both end surfaces, the disc-shaped magnet members being arranged alternately with the disc-shaped yokes in the hollow cylindrical case such that the magnetic poles having the same polarity of the adjacent disc-shaped magnet members face each other via each disc-shaped yoke; and (d) a pair of end covers made of a corrosion-resistant, non-magnetic material, each end cover being fixed to each end of the hollow cylindrical case so that the inside of the hollow cylindrical case is sealed.

1 Claim, 3 Drawing Sheets

MAGNET ARTICLE FOR ATTRACTING FOREIGN MATTERS IN THE STOMACH

BACKGROUND OF THE INVENTION

The present invention relates to a magnet article for attracting foreign matters such as magnetically attractable matters in the shape of nail, wire, needle, power, etc. in the stomachs of ruminants such as cows.

Typical ruminants such as cows grazing in a field have ruminant stomachs and tend to swallow grass or hay without sufficient mastication. Accordingly, if there are nails, needles, wires, magnetic powders, etc. in the feeds, they would be swallowed together with the feeds into the rumen and the second stomach. If this happens, the stomach is damaged, causing various troubles such as gastritis, dyspepsia, etc. As a result, the cows die in an extreme case.

To prevent such incidents, the feeds supplied to the cows are usually examined to detect metallic foreign matters, particularly iron articles, and the fields are also examined to detect such metallic foreign matters. Despite such examination, it has been impossible to completely prevent the cows from swallowing metallic foreign matters. Accordingly, rod-shaped permanent magnets are conventionally swallowed into the second stomachs of the cows in order to attract magnetically attractable matters accidentally taken by the cows. This procedures prevent the magnetically attractable matters from sticking the gastric mucosae of the cows.

Conventionally used as magnet articles for attracting foreign matters in the stomachs are rod-shaped Alnico magnets having magnetic poles on both end surfaces. However, since these rod-shaped Alnico magnets have magnetic poles on both ends, they do not have an attraction force in their middle portions. As a result, metal pieces such as nails, needles, etc. are attracted predominantly to both ends of the rod-shaped Alnico magnets, and rather cause damage to the gastric mucosae. In addition, since the ends of Alnico magnets have round surfaces to protect the gastric mucosae, metal pieces attracted to the Alnico magnets are extremely unstable, so that the attraction force of the magnets cannot fully be utilized.

There are also rod-shaped Alnico magnets having a plurality of magnetic poles along their cylindrical surfaces, for instance, eight magnetic poles extending longitudinally on their cylindrical surfaces. These rod-shaped magnets show higher attraction force than those having a pair of magnetic poles on both ends. However, they do not have sufficiently high surface magnetic flux density due to small coercive forces thereof. In addition, since demagnetization takes place due to the contact of metal pieces attracted to the rod-shaped magnets, the magnets fail to keep the metal pieces attracted thereto, permitting the metal pieces to move into the subsequent stomachs.

To obviate such problems, proposals have been made to provide a magnet article for attracting foreign matters in the stomach, which comprises a plurality of disc-shaped magnet members having opposing magnetic poles on both end surfaces and arranged coaxially such that the magnetic poles having the same polarity face each other between the adjacent permanent magnets (for instance, Japanese Utility Model Publication No. 57-53550 and Japanese Utility Model Laid-Open No. 60-61703).

These magnet articles have a plurality of magnetic poles in their intermediate portions in addition to their end portions, so that even elongated metal pieces can be attracted thereto along their lengths. As a result, the gastric mucosae are prevented from being sticked by metal pieces.

However, those proposed by the above Japanese references are made of ferrite magnets, failing to show sufficient magnetic forces. Specifically, these magnet articles show surface magnetic flux densities of only 1600–1800 G, which make the magnet articles unable to attract and keep elongated metal pieces completely along their lengths. As a result, it is impossible to keep the elongated metal pieces from sticking the gastric mucosae completely.

In addition, since porous ferrite magnets are exposed to a gastric juice in these magnet articles, they are eroded by the gastric juice. As a result, their service lives are relatively short.

Incidentally, even if the ferrite magnets are replaced by the Alnico magnets, the service lives of the magnet articles cannot be sufficiently elongated, and their fabrication becomes rather complicated. In addition, since the Alnico magnets show smaller coercive forces than the ferrite magnets, the magnet articles constituted by the Alnico magnets cannot show as high magnetic forces as the ferrite magnets.

OBJECT AND SUMMARY OF THE INVENTION

Accordingly, an object of the present invention is to provide a magnet article for attracting foreign matters in the stomach, which is free from the above problems, thereby enjoying an extremely long service life with a large attraction force.

The magnet article for attracting foreign matters in the stomach according to the present invention comprises:

(a) a hollow cylindrical case made of a corrosion-resistant, non-magnetic material;

(b) a plurality of disc-shaped yokes made of a soft magnetic material;

(c) a plurality of disc-shaped magnet members made of an R—Fe—B type permanent magnet material, wherein R represents one or more rare earth elements, each of the disc-shaped magnet members having magnetic poles on both end surfaces, the disc-shaped magnet members being arranged alternately with the disc-shaped yokes in the hollow cylindrical case such that the magnetic poles having the same polarity of the adjacent disc-shaped magnet members face each other via each disc-shaped yoke; and (d) a pair of end covers made of a corrosion-resistant, non-magnetic material, each end cover being fixed to each end of the hollow cylindrical case so that the inside of the hollow cylindrical case is sealed.

DETAILED DESCRIPTION OF THE INVENTION

Figure 1:
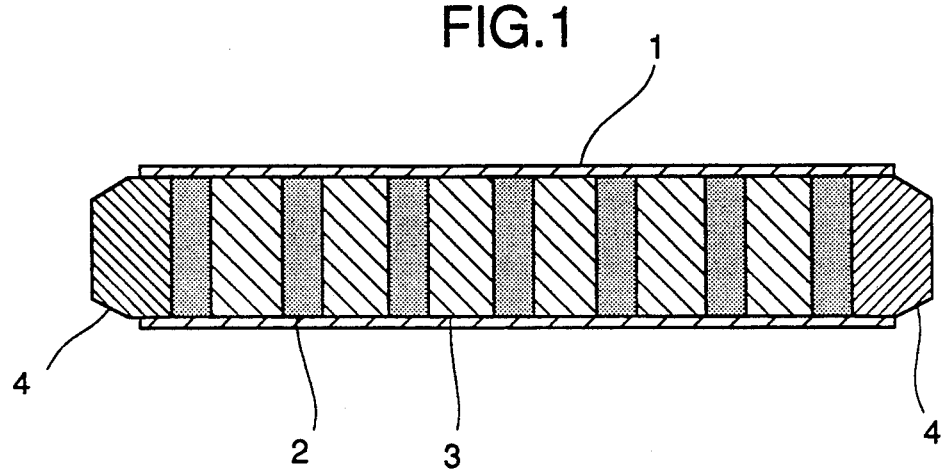
FIG. 1 is a cross-sectional view showing the magnet article according to one embodiment of the present invention.

FIG. 1 show a magnet article comprising a hollow cylindrical case 1 made of a corrosion-resistant, non-magnetic material, a plurality of disc-shaped magnet members 2, 2, . . . made of an R—Fe—B type permanent magnet material, a plurality of disc-shaped yokes 3, 3, . . . made of a soft magnetic material, and a pair of end covers 4, 4 made of a corrosion-resistant, non-magnetic material.

The disc-shaped magnet members 2 are made of an R—Fe—B type permanent magnet material, wherein R represents one or more rare earth elements. The rare earth elements are typically Nd and Pr. The content of the rare earth elements R is preferably 10–30 atomic %. When it is less than 10 atomic %, the R—Fe—B type permanent magnet material shows poor magnetic properties, particularly coercive force. On the other hand, when it is higher than 30 atomic %, an R-rich, non-magnetic phase is generated excessively, resulting in the decrease in a residual magnetic flux density. To improve the coercive force, part of Nd (about 1–30%) may be substituted with heavy rare earth elements such as Dy, Ho and Tb. Further, R may include at least one of La, Ce, Sm, Gd, Er, Eu, Tm and Y.

The content of Fe is preferably 65–85 atomic %. When the content of Fe is smaller than 65 atomic %, the R—Fe—B type permanent magnet material shows a poor residual magnetic flux density. On the other hand, when it is higher than 85 atomic %, the R—Fe—B type permanent magnet material shows a poor coercive force.

The remaining part of the R—Fe—B type permanent magnet material is substantially B. The content of B is preferably in the range of 2–28 atomic %. When B is less than 2 atomic %, the magnet has a low coercive force, and when B is more than 28 atomic %, the magnet contains a B-rich, non-magnetic phase in a large amount and has a low residual magnetic flux density. In addition to the above indispensable elements, additional elements such as Co, Al, Ti, etc. may be contained. Also, inevitable impurities such as oxygen may be contained in permissible amounts. R—Fe—B type permanent magnet materials containing such elements are disclosed by U.S. Pat. No. 4,888,068.

The disc-shaped magnet members may be produced as follows: First, an R—Fe—B alloy is melted in Ar or in vacuum by a usual method. In this case, B may be added as ferroboron. The rare earth element is preferably added last. An ingot prepared by melting the R—Fe—B alloy is pulverized coarsely and then finely. The coarse pulverization is conducted by a stamp mill, a jaw crusher, a Brown mill, a disc mill, etc. The fine pulverization is conducted by a jet mill, a vibration mill, a ball mill, etc. In both cases, a non-oxidizing atmosphere is used to prevent the oxidation of the R—Fe—B alloy. For this purpose, the pulverization is conducted in an organic solvent or in an inert gas. The particle size after pulverization is preferably 2–5 μm.

Magnet powder thus prepared is formed into a desired shape in a magnetic field by a die. The resulting green body (compact) is then sintered in an inert gas such as Ar, He, etc., or in vacuum or in hydrogen at 950°–1150° C. for 20 minutes to 2 hours. After the sintering, a heat treatment is conducted in an inert gas atmosphere, if necessary. The preferred heat treatment conditions are 500°–700° C. and 30 minutes to 3 hours. Finally, magnetization is conducted along the direction of magnetic powder orientation (in this case thickness direction). The intensity of a magnetization field is preferably 20–30 kOe.

The disc-shaped magnet members 2, 2, . . . are arranged alternately with disc-shaped yokes 3, 3, . . . . The disc-shaped yokes 3, 3, . . . are made of a soft magnetic material such as soft steel, silicon steel and Permalloy. In this case, the disc-shaped magnet members 2, 2, . . . should be arranged such that the magnetic poles having the same polarity face each other via the disc-shaped yoke 3 between the adjacent disc-shaped magnet members 2, 2. By this arrangement, a high surface magnetic flux density can be obtained along the entire length of the magnet article.

The disc-shaped magnet members 2, 2, . . . and the disc-shaped yokes 3, 3, . . . arranged alternately with each other are inserted into the hollow cylindrical case 1 made of a corrosion-resistant, non-magnetic material. The corrosion-resistant, non-magnetic material may be stainless steel, resin-coated aluminum alloy, copper alloy (bronze), etc.

Both ends of the hollow cylindrical case 1 are sealed by end covers 4, 4 made of a corrosion-resistant, non-magnetic material. This corrosion-resistant, non-magnetic material may be the same as above. Each end cover 4 is liquid-tightly fixed to the hollow cylindrical case 1 to seal the inside of the hollow cylindrical case 1. As a result, the disc-shaped magnet members 2, 2, . . . are protected from the gastric juice. The fixing of the cover 4 to the hollow cylindrical case 1 is conducted by pressing the end cover 4 into the hollow cylindrical case 1, or by using a slightly larger hollow end cover 4 and inserting the hollow cylindrical case 1 into the hollow end cover 4. If necessary, an adhesive may be used to completely bond the end cover 4 to the hollow cylindrical case 1.

In the present invention, the magnet article generally has a shape having a length of 6–8 cm, and an outer diameter of 1.0–3.0 cm. Because there is a repulsive force between the adjacent disc-shaped magnet members 2, 2, it is preferable to use an adhesive to bond each disc-shaped magnet member 2 and each disc-shaped yoke 3.

The present invention will be explained in further detail by way of the following Examples.

EXAMPLE 1, COMPARATIVE EXAMPLES 1 AND 2

The magnet article having a structure shown in FIG. 1 was produced from a hollow cylindrical case 1 made of stainless steel (SUS 304) and having an outer diameter of 16 mm, an inner diameter of 14 mm and a length of 74 mm; disc-shaped magnet members 2, 2, . . . made of an Nd—Fe—B type permanent magnet (HS-30BV," manufactured by Hitachi Metals, Ltd.) and having an outer diameter of 14 mm and a thickness of 4 mm and having opposing magnetic poles on both end surfaces; disc-shaped yokes 3, 3, . . . made of soft steel ("SS-41") and having an outer diameter of 14 mm and a thickness of 6.5 mm; and a pair of frustoconical end covers 4, 4 made of stainless steel and having an outer diameter of 14 mm and a thickness of 6.5 mm. The assembling of this magnet article was carried out by pressing one end cover 4 into one end of the hollow cylindrical case 1, inserting the disc-shaped magnet members 2, 2, . . . and the disc-shaped yokes 3, 3, . . . alternately such that the magnetic poles having the same polarity faced each other between the adjacent disc-shaped magnet members 2, 2, . . . and finally pressing the other end cover 4 into the other end of the hollow cylindrical case 1.

For comparison, the same magnet articles were produced except for using as disc-shaped magnet members 2, 2, . . . , ferrite magnets ("YBM-2B" manufactured by Hitachi Metals, Ltd., Comparative Example 1) and Alnico magnets ("YCM-1B" manufactured by Hitachi Metals, Ltd., Comparative Example 2).

Figure 3:
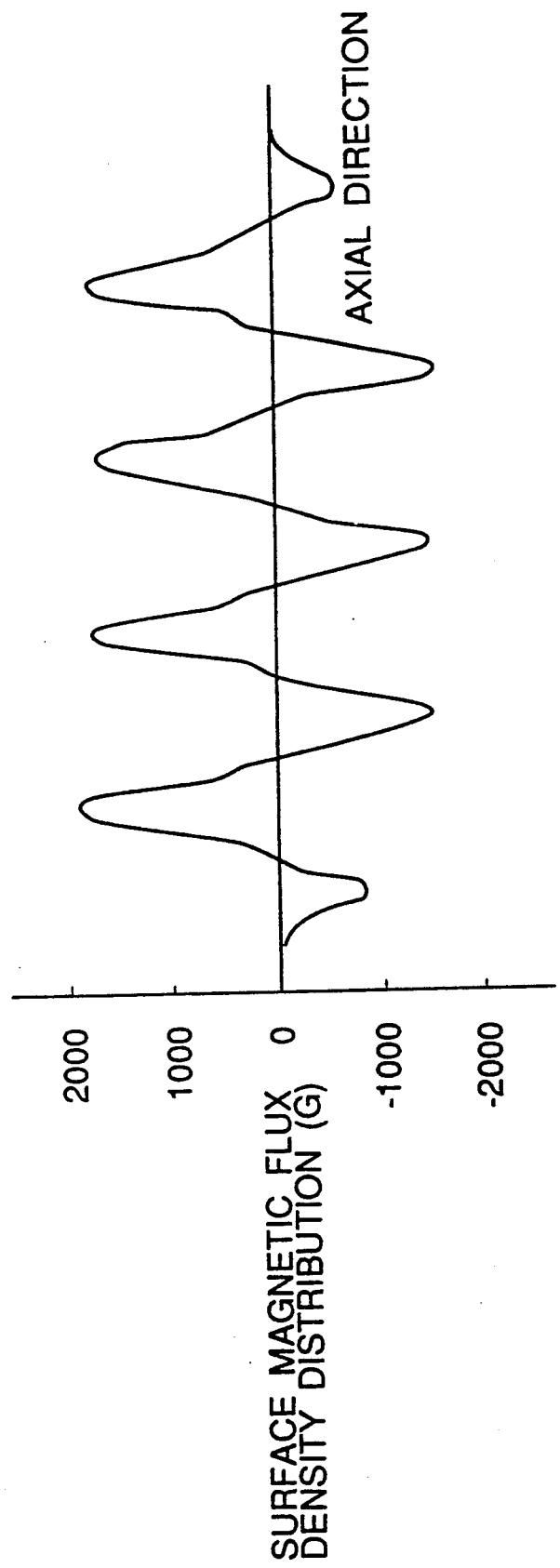
FIGS. 3 and 4 are graphs each showing the relation between a surface magnetic flux density and an axial position in the magnet article of Comparative Example.
Figure 4:
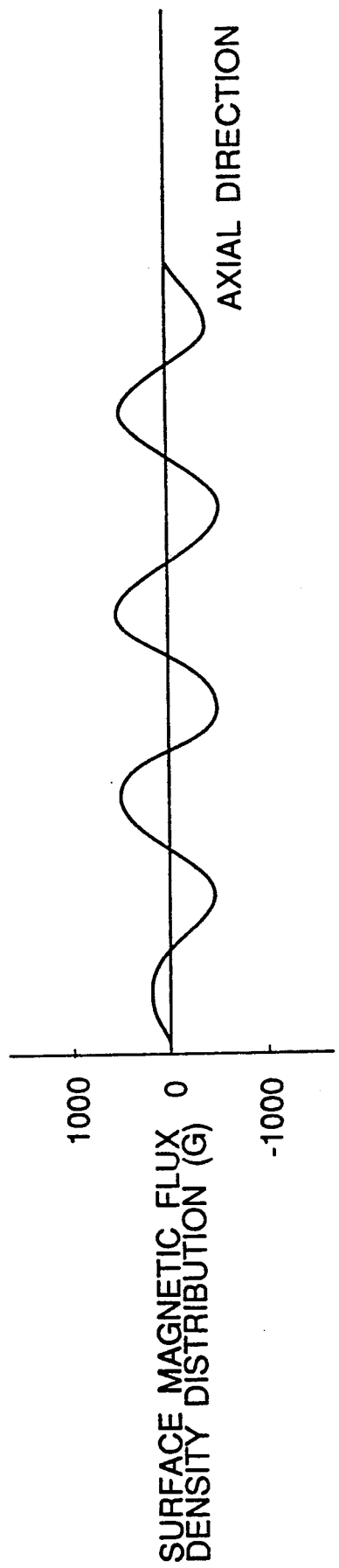

All of these magnet articles were examined with respect to a surface magnetic flux density. The results are shown in FIGS. 2-4.

Figure 2:
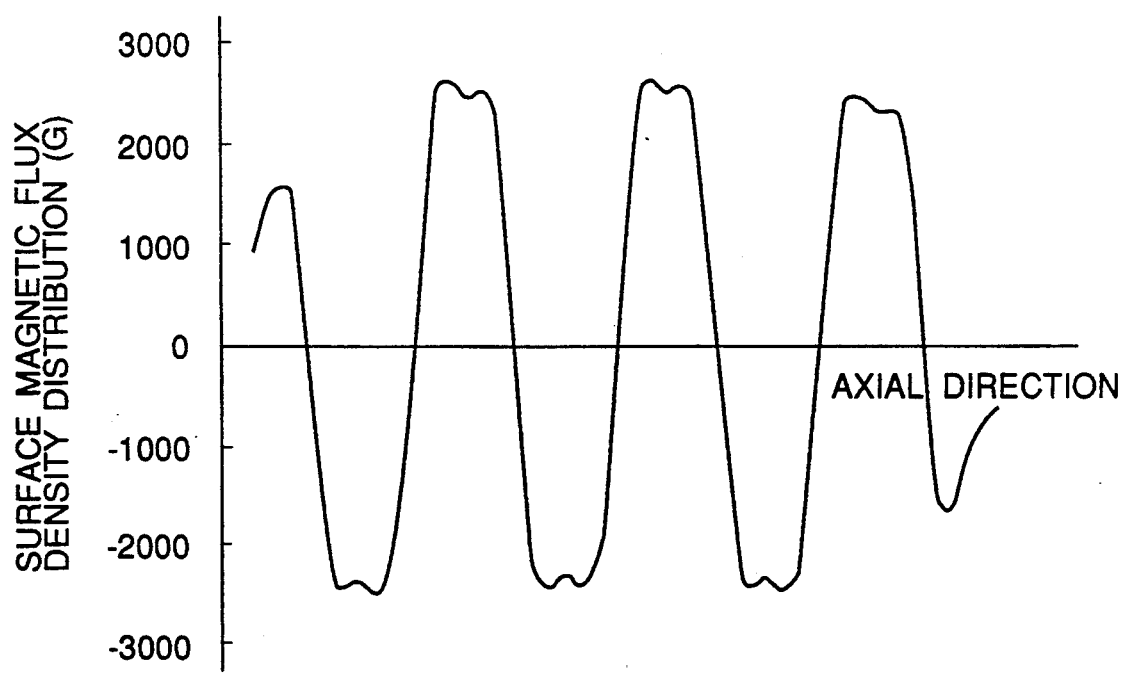
FIG. 2 is a graph showing the relation between a surface magnetic flux density and an axial position in the magnet article according to one embodiment of the present invention.

FIG. 2 shows that the magnet article of the present invention has a surface magnetic flux density whose peak values are as high as 2600-3000 G. This level is sufficient to completely attract and remove metal pieces taken into the stomach. On the other hand, the magnet article containing ferrite magnets (Comparative Example 1) has a surface magnetic flux density whose peak values are only 1600-1800 G. This level of surface magnetic flux density is insufficient to completely attract and remove metal pieces taken into the stomach. Incidentally, the magnet article containing Alnico magnets (Comparative Example 2) has a surface magnetic flux density whose peak values are only 500 G or so. This level of a surface magnetic flux density is extremely low to attract and remove the metal pieces.

Next, these magnet articles were given to cows to examine whether magnetically attractable matters such as nails could be removed from their stomachs. As a result, it was found that the magnet article of Alnico magnets failed to completely remove the magnetically attractable matters from the stomachs. With respect to the magnet article of ferrite magnets, better results were obtained, but it showed poor corrosion resistance to the gastric juice. On the other hand, the magnet article of the present invention showed not only excellent performance of attracting and removing the magnetically attractable matters from the stomachs but also excellent corrosion resistance to the gastric juice.

In order to quantitatively evaluate the corrosion resistance of each magnet article, an acceleration test was conducted by using a hydrochloric acid. As a result, it is expected that the magnet article of ferrite magnets shows a service life of 6-24 months or so. On the other hand, it is expected that the magnet article of the present invention shows a service life as long as 8-10 years.

Although the above Example uses stainless steel as a corrosion-resistant, non-magnetic material, any other corrosion-resistant, non-magnetic materials may be used. With respect to the end covers, they may be in any other shapes. For instance, they may have a hollow shape into which the hollow cylindrical case is pressed for tight sealing. Of course, the disc-shaped magnet members and the disc-shaped yokes may be bonded to each other with an adhesive.

As mentioned above in detail, since the magnet article of the present invention has a larger surface magnetic flux density in its intermediate portion than in its end portions, elongated foreign matters such as nails, needles, wires, etc. can be attracted to the magnet article along its length, thereby preventing these foreign matters from sticking to the gastric mucosae. Since the disc-shaped magnet members are made of R—Fe—B type permanent magnet materials, a much larger surface magnetic flux density can be obtained than in a case where the disc-shaped magnet members are made of ferrite magnets or Alnico magnets. Accordingly, complete removal of foreign matters from the stomach can be achieved. Also, since the disc-shaped magnet members and the disc-shaped yokes are sealed in a container consisting of the hollow cylindrical case and the end covers, the magnet article is highly durable in the gastric juice. Therefore, it can be used without any corrosion problem during the entire life spans of the cows.

What is claimed is:

1. A magnet article for attracting foreign matters in the stomach comprising:
   (a) a hollow cylindrical case made of a corrosion-resistant, non-magnetic material;
   (b) a plurality of disc-shaped yokes made of a soft magnetic material;
   (c) a plurality of disc-shaped magnet members made of an R—Fe—B permanent magnet material, wherein R represents one or more rare earth elements, each of said disc-shaped magnet members having magnetic poles on both end surfaces, said disc-shaped magnet members being arranged alternately with said disc-shaped yokes in said hollow cylindrical case such that the magnetic poles having the same polarity of the adjacent disc-shaped magnet members face each other via each disc-shaped yoke; and
   (d) a pair of end covers made of a corrosion-resistant, non-magnetic material, each end cover being fixed to each end of said hollow cylindrical case so that the inside of said hollow cylindrical case is sealed.

* * * * *